United States Patent
DeKalb et al.

[11] Patent Number: 5,865,813
[45] Date of Patent: Feb. 2, 1999

[54] INTRAVENOUS TUBE OCCLUDER

[75] Inventors: Shawn DeKalb; Gary Bell, both of San Diego; Robert M. Cunningham, Carlsbad, all of Calif.

[73] Assignee: Alaris Medical Systems, Inc., San Diego, Calif.

[21] Appl. No.: 502,747

[22] Filed: Jul. 14, 1995

[51] Int. Cl.[6] .................................................. A61M 5/00
[52] U.S. Cl. ........................................................... 604/250
[58] Field of Search ................................. 604/246, 250; 251/7, 9, 10

[56] References Cited

U.S. PATENT DOCUMENTS

| | | | |
|---|---|---|---|
| 207,469 | 8/1878 | Wolf | 251/9 |
| 1,344,433 | 6/1920 | Blackburn | 251/9 |
| 2,889,848 | 6/1959 | Redmer | 137/315 |
| 3,189,038 | 6/1965 | Peckmann | 137/315 |
| 3,926,175 | 12/1975 | Allen et al. | 251/7 |
| 4,247,076 | 1/1981 | Larkin | 251/7 |
| 4,586,691 | 5/1986 | Kozlow | 251/7 |
| 4,610,664 | 9/1986 | Harle | 251/9 |
| 4,689,043 | 8/1987 | Bisha | 604/280 |
| 5,083,741 | 1/1992 | Sancoff | 251/9 |
| 5,238,218 | 8/1993 | Mackal | 604/250 |
| 5,423,769 | 6/1995 | Jonkman et al. | 6040/250 |

Primary Examiner—Manuel Mendez
Attorney, Agent, or Firm—Pennie & Edmonds LLP

[57] ABSTRACT

An IV tube occluder is disclosed which has a bow portion and a linkage portion which act to occlude an IV tube to prevent unwanted flow of liquid to a patient. The linkage portion and bow portion are engaged to allow the ends of the linkage portion to rotate within a certain range. The linkage portion has an extending pinching member which is used to occlude a portion of flexible tubing by pressing the tube against the bow portion. The pinching member of the linkage portion moves against the bow portion through the provision of a hinge portion of the linkage portion, which allows the pinching member to hold the tube in an open or closed position. In an alternative embodiment, both the bow portion and linkage portion are formed as a continuous body.

20 Claims, 5 Drawing Sheets

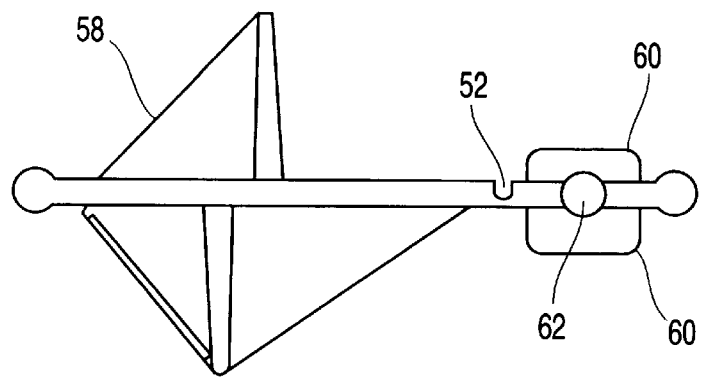
FIG. 9
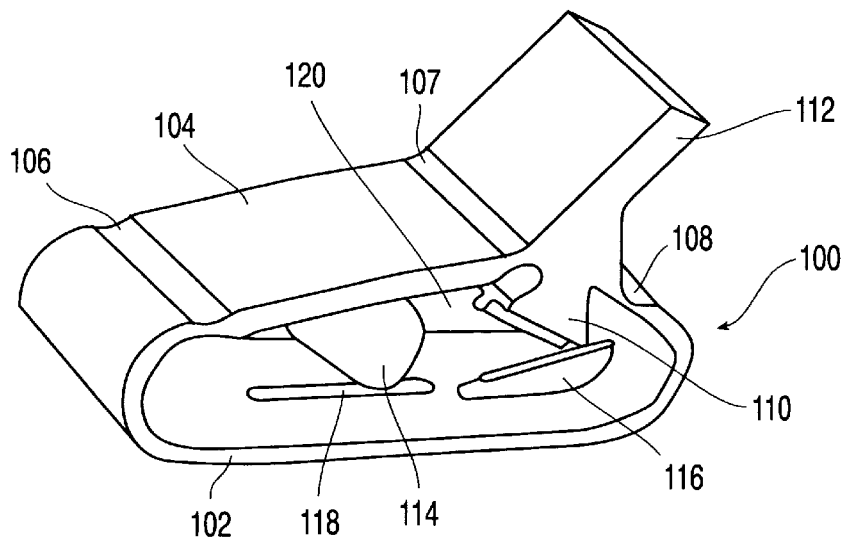
FIG. 10
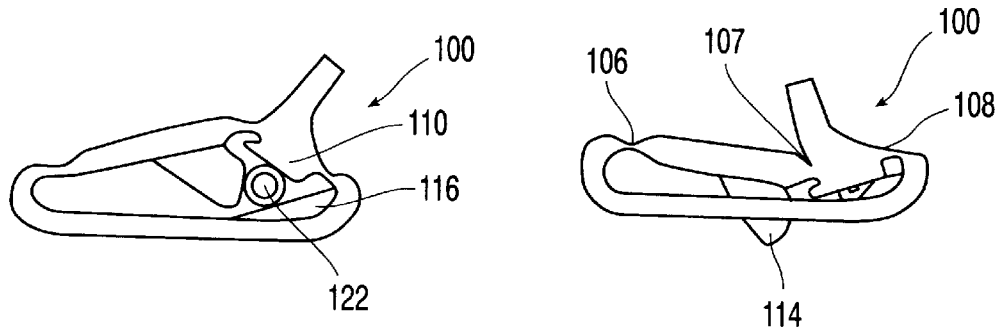
FIG. 11  FIG. 12

INTRAVENOUS TUBE OCCLUDER

BACKGROUND OF THE INVENTION

The present invention generally relates to occluders for flexible tubing that prevent fluid flow through a portion of tubing. The present invention specifically relates to the selective occluding of an intravenous (IV) tube used to infuse liquid medication to a patient.

Intravenous infusion of medical solutions to patients is ell known in the medical profession. Such infusions typically use a pump, such as a peristaltic pump, to create a moving zone of occlusion along a portion of an IV tube to administer fluid to a patient. The danger inherent in the use of the IV tube with a pump is that unwanted fluid will flow to the patient. Typically, the times of greatest concern for this danger are during the initial set-up of the IV administration system and at any subsequent time when the IV tube is connected between the fluid source and the patient and the IV tube becomes disengaged from the device for some reason.

Various devices to constrict or occlude flow of liquid through tubes are described in the prior art. Typical devices include manually operated slide clamps. Roller clamps, such as the one described in U.S. Pat. No. 3,189,038, are one such example. A slide clamp of typical design is also described in U.S. Pat. No. 2,889,848. Both of these clamps are multi-element assemblies and both must be activated independently and separately from any medical device which may be operatively attached to the IV fluid line.

The need to coordinate the operation of a clamp or occluder with an associated medical device, such as a peristaltic pump has been recognized in the prior art as well. U.S. Pat. No. 4,586,691 discloses a safety slide clamp that requires the cooperation of structure between the device and the slide clamp itself. Another prior art slide clamp for an IV tube associated with an IV infusion pump is disclosed in U.S. Pat. No. 4,689,043. This device includes a peristaltic pump enclosed in a housing with a door and a door mounted handle for operatively engaging and disengaging the slide clamp. The disclosed clamp, however, includes several elements, each of which may require precision machine tolerances.

A product available from Medex Inc., known as the Trilogy™ Multichannel Infusion Pump, includes an optional flow clip on the disposable IV administration sets for use with the infusion pump. The flow clamp is a single piece of deformable plastic with two extending members that must be spread apart by the pump to open the tube, similar to a clothespin arrangement. In the relaxed state, the flow clamp occludes all flow of liquid through the tube. This structure is difficult to adapt for manual use, due to the fact that it is more difficult to spread two members apart, rather than pushing them together. In addition, the default to occluding the tube may lead to the permanent deformation of both the clamp and the tube itself.

SUMMARY OF THE INVENTION

In light of the above-described needs, it is an object of the present invention to provide an occluder for use with flexible tubing that is relatively cost-effective and may be used in conjunction with common infusion pump apparatus.

It is a further object of the present invention to provide an occluder that can be alternatively used manually when disengaged from an infusion pump apparatus.

It is a further object of the invention to provide an occluder that is stable in both an open and closed (occluding) configuration.

These and other objects are met according to the present invention by a tube occluder which includes a bow portion having two ends, and a linkage portion having two ends, with the ends of the bow portion and linkage portion being engaged to define a passageway between the bow portion and the linkage portion. It is through this defined passageway that the tube to be occluded will be located. The ends of the bow portion and linkage portion are joined through a snap-fit arrangement, in which the ends of the linkage portion are substantially cylindrical, and the ends of the bow portion have appropriately designed receptacles.

The linkage portion has a pinching member extending from the linkage portion into the passageway between said bow portion and said linkage portion, which will apply pressure to the tube to occlude it. The linkage portion further comprises a hinge portion, the hinge portion being adapted to allow the pinching member to move closer to the bow portion and occlude the tube.

The hinge portion, in the preferred embodiment, includes a "living hinge". The living hinge is constructed by creating an area of reduced thickness along the linkage portion. The linkage portion has a generally uniform thickness, except for the area desired to be the hinge portion. The reduced thickness allows the resilient material of the linkage portion to bend in both directions, which further allows the extending pinching member to move in relation to the bow portion and occlude the tube when desired.

The tube occluder also may include a tube guide portion extending from the bow portion to direct a tube through a passage defined by said bow portion and linkage portion. The tube guide comprises a circular portion which is extended from the bow portion in the perpendicular plane. The piece of tubing to be occluded is threaded through the guide portion, which will place the section of the tube to be occluded in the opening between the bow and linkage portions, and proximate to the pinching member.

An alternative embodiment of the occluder is possible in which both the bow portion and the linkage portion are formed as a continuous body. The alternative occluder includes three living hinges, using two hinges to replace the snap-fit arrangement between the ends of the bow portion and linkage portion. The alternative occluder has an actuating member which extends from the linkage portion, away from the bow portion, and allows either manual or automatic depression in cooperation with an infusion pump apparatus. The actuating member acts on a pinching member which extends downward from the linkage member and presses against a tube.

The alternative occluder also has a tube guide member of a different design. The tube guide member is in the shape of a blade which extends downward from the linkage member into the passageway defined by the bow portion and linkage portion. The tube guide member prevents the tube from slipping away from the pinching member, and as the actuator member is depressed, the tube guide member slides through an appropriately sized longitudinal slot in the bow portion. Once the actuator member has been depressed and the occluder is in the closed position, it is stable and will keep the tube occluded until an additional force is applied to open the tube.

BRIEF DESCRIPTION OF THE DRAWINGS

These and other objects of the invention will become more readily apparent from the following detailed description, which should be read in conjunction with the accompanying drawings, in which:

FIG. 9 is a side view of an alternative embodiment of the linkage portion of the occluder;

FIG. 10 is a perspective view of an alternative embodiment of the occluder;

FIG. 11 is a side elevational view of an alternative embodiment of the occluder in the open position; and FIG. 12 is a side elevational view of an alternative embodiment of the occluder in the closed position.

DETAILED DESCRIPTION

Figure 1:
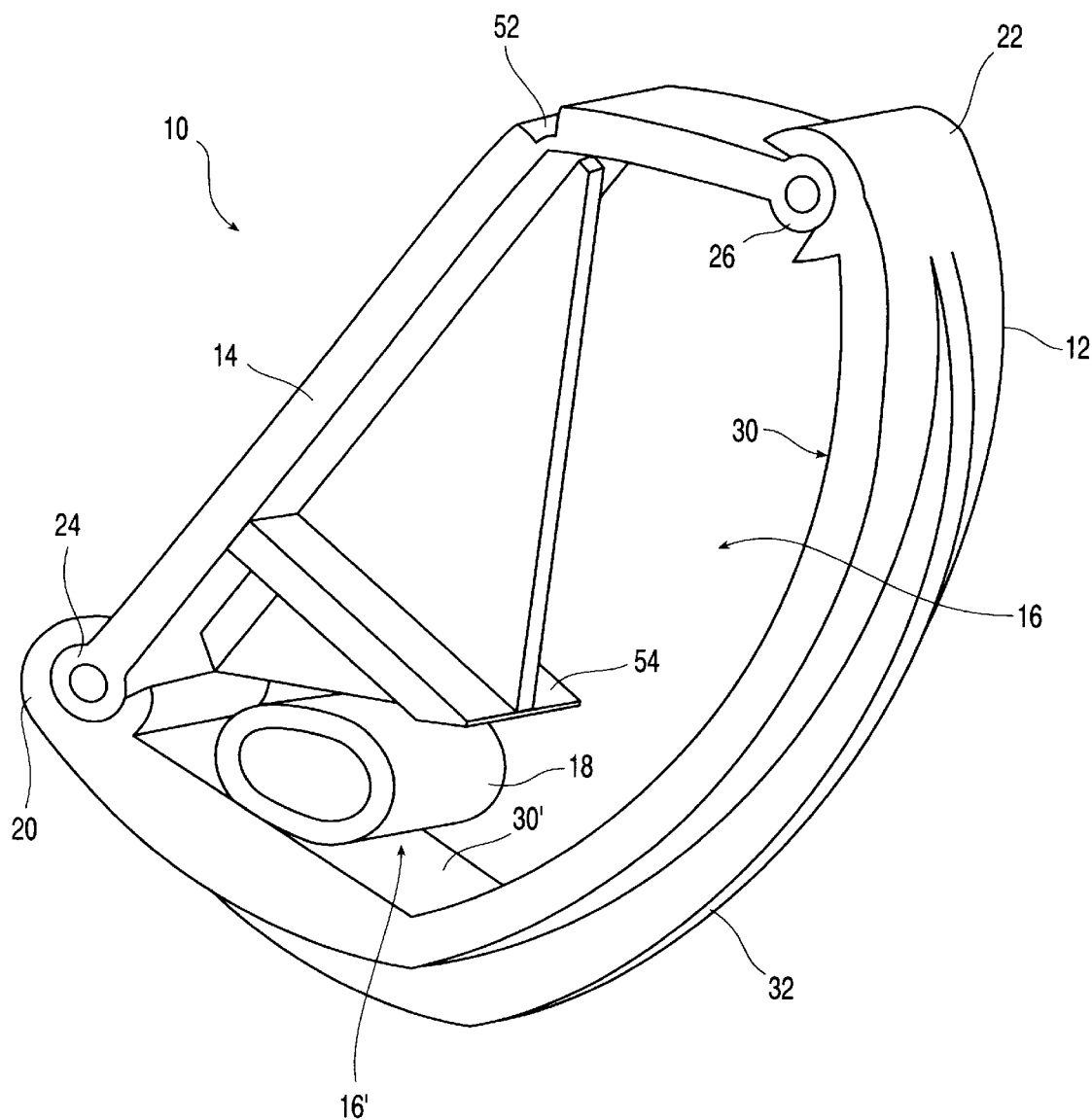
FIG. 1 is a perspective view of the occluder in the open position.
Figure 2:
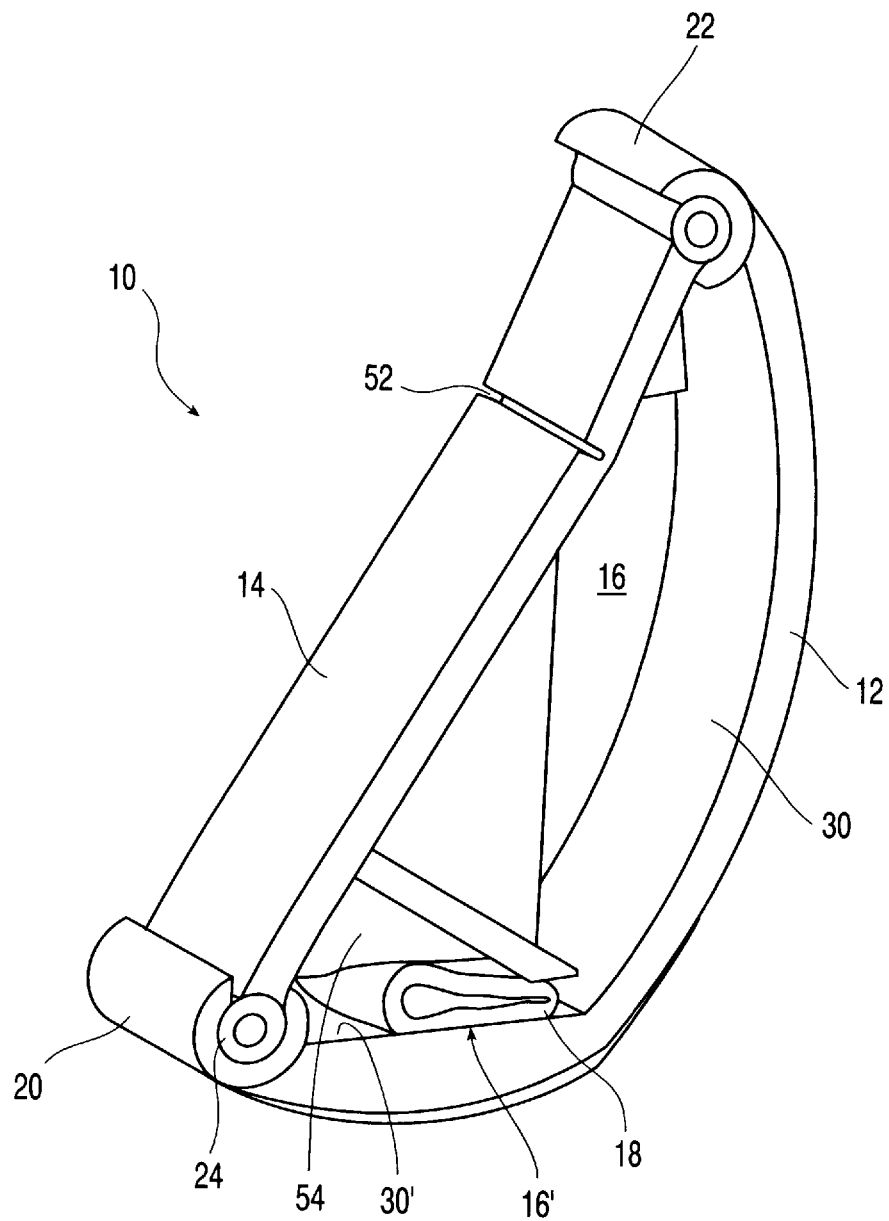
FIG. 2 is a perspective view of the occluder in the closed position.

A preferred embodiment of occluder 10 of the present invention is shown in FIG. 1. The occluder 10 has a bow portion 12 and a linkage portion 14. Linkage portion 14 fits into bow portion 12 through a snap fit arrangement. The snap fit arrangement is provided by two ends 20, 22 of bow portion 12 which have openings that mate with extensions 24, 26 on both ends of linkage portion 14. The design of the snap-fit, in conjunction with the hinge design allows the ends of the linkage portion 14 to rotate so as to allow the occlusion of a portion of flexible tubing. The bow portion 12 and linkage portion 14, when snapped together, create a passageway (labeled as 16) which will vary as the linkage portion 14 is manipulated. A section of flexible tubing 18 to be occluded is shown in FIGS. 1–2, to demonstrate the operation of the occluder, which will be discussed in more detail below, following a description of the structure of bow portion 12 and linkage portion 14.

Figure 3:
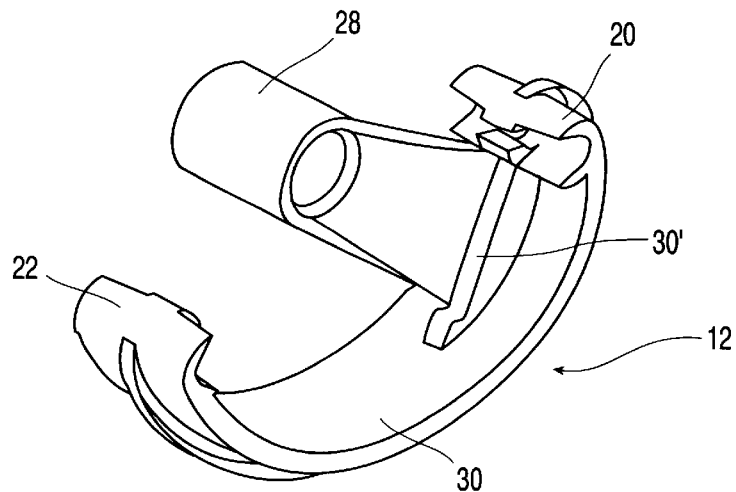
FIG. 3 is a perspective front view of the bow portion of the occluder.
Figure 4:
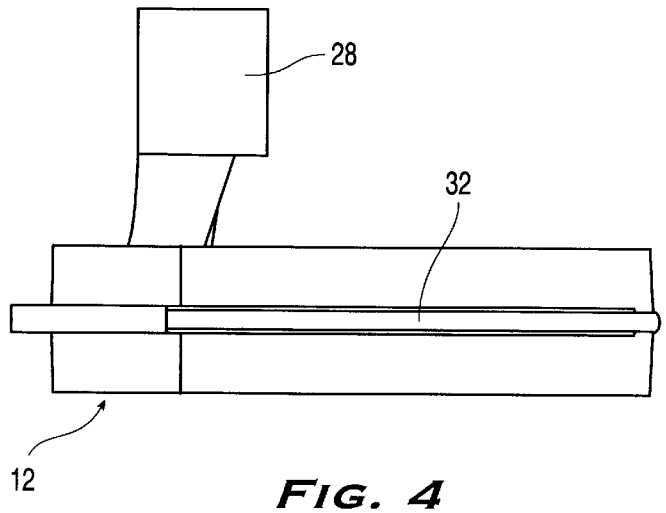
FIG. 4 is a bottom plan view of the bow portion of the occluder.
Figure 5:
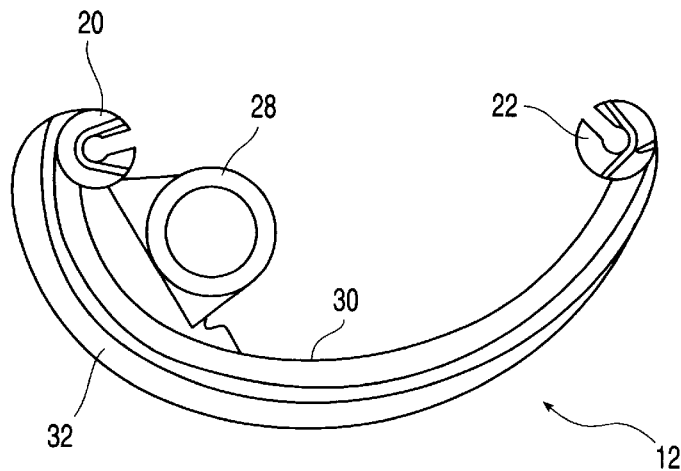
FIG. 5 is a side view of the bow portion of the occluder.

Bow portion 12 is illustrated in FIGS. 3–5. As shown, bow portion 12 has two ends 20, 22, adapted to receive the two ends 24, 26 of the linkage portion 14. The openings at the ends 20, 22 of the bow portion 12 are curved to allow the generally cylindrical or slightly conical extensions at the ends 24, 26 of the linkage portion 14 to rotate within a limited range within the openings. In addition, bow portion 12 preferably has an extending tube guide 28, which acts to guide tube 18 into the exclusion section 16' of passageway 16 formed between bow portion 12 and linkage portion 14. Tube guide 28 has a circular portion and an extending portion that is attached to one side of the circular portion and leads to the bow portion. Preferably, the inner diameter of guide 28 provides a snug fit to the tube to enhance bonding to the tube. More preferably, the guide inner diameter will increase and flatten as it nears the pinch off location. Although preferred, tube guide 28 is not strictly required and it is not shown in FIGS. 1–2 for purposes of clarity of the drawings. The tube should, however, pass through occlusion section 16'.

Inside surface 30 of the bow portion, which is preferably of smooth construction, includes a preferably flat portion 30' of the bow that tube 18 is pressed against when occluded. Bow portion 12 additionally has a substantially longitudinal rib 32 along its outside surface. Rib 32 provides additional structural integrity to bow portion 12 by distributing bending stresses and strain along the length of the bow, particularly at times of highest stress when the hinge snaps across center. Also, rib 32 can be specially adapted for use of the occluder in conjunction with an infusion pump apparatus.

Figure 6:
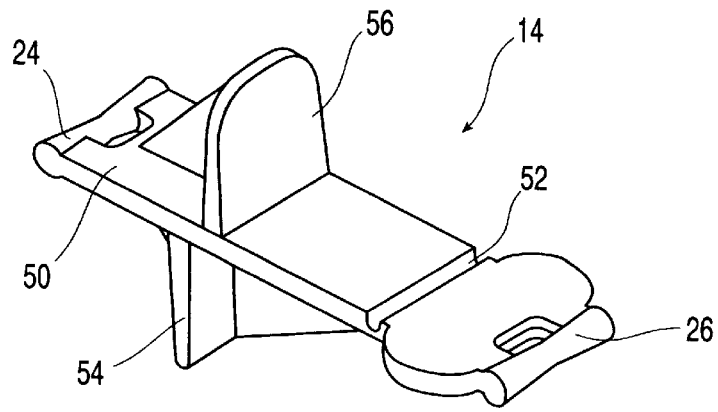
FIG. 6 is a perspective view of the linkage portion of the occluder.
Figure 7:
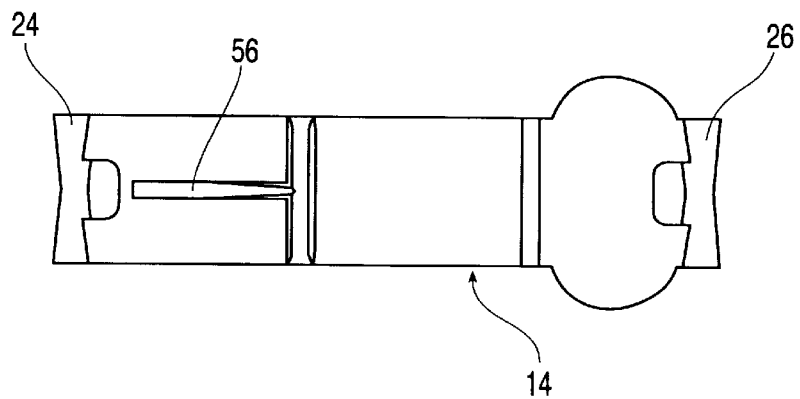
FIG. 7 is a top plan view of the linkage portion of the occluder.
Figure 8:
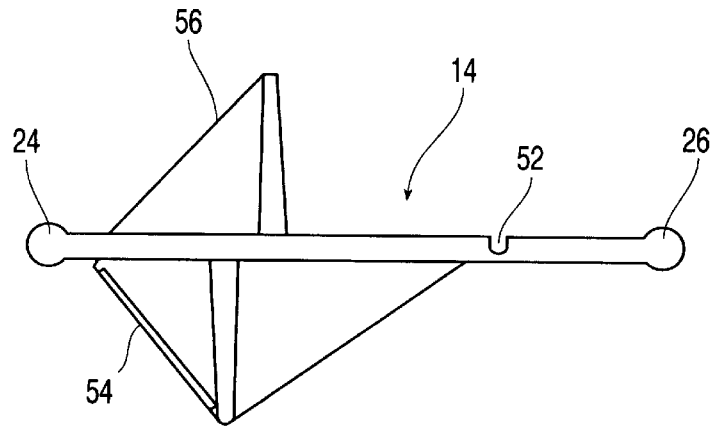
FIG. 8 is a side view of the linkage portion of the occluder.

The linkage portion 14 is shown in FIGS. 6–8. As illustrated, linkage portion 14 has two generally cylindrical or slightly conical elements at ends 24, 26 which snap into the mating openings 20, 22 of bow portion 12 as described above. The linkage portion has a generally flat base 50, which is of uniform thickness excepting hinge portion 52. Hinge portion 52 is an area of reduced thickness, which, due to the resiliency of the material, provides a living hinge which will allow the linkage portion 14 to bend in two directions, inward towards the bow portion, and outward away from the bow portion.

Linkage portion 14 includes pinching member 54, which acts against the portion of tubing to be occluded. An actuator member 56 may be further provided on the linkage member to facilitate a user depressing the linkage member towards bow portion 12.

The bow portion of the occluder can be manufactured of any substantially rigid material, for example, plastics such as Terlux™, which is a trade name for a MABS material sold by BASF. The material selected should permit some deflection of the bow portion to provide the driving force for tube occlusion as explained below. The linkage portion can be manufactured out of any sufficiently deformable yet resilient material that will allow the creation of the living hinge by forming a portion of the linkage that has a reduced thickness. A suitable material for this purpose is high density polyethylene (HDPE), but any similar material, such as polypropylene, could be used.

An alternative embodiment of the linkage is shown in FIG. 9. The alternative linkage has additional members 60, 62. Stabilizing members 60 are provided as a structural variation to add rigidity to the linkage member 14 near the location of hinge portion 52. Pump actuation member 62 has a cylindrical cross section and is provided to facilitate cooperation between occluder 10 and the structure of a pump when used in conjunction with an infusion pump apparatus.

Returning to FIGS. 1–2, the operation of the occluder 10 will be described in greater detail. As noted above, FIGS. 1 and 2 do not show the tube guide 28, or the actuator member 56 for the purposes of clarity. FIG. 1 shows the open position of the occluder 10. As illustrated, in the open position living hinge portion 52 is bent so that the linkage portion 14 is bent away from bow portion 12. In particular, the pinching member 54 is not occluding the tube 18 due to the position of linkage member 14.

FIG. 2 shows the closed position of occluder 10, in which pressure has been applied to the linkage member 14, forcing the hinge portion 52 to bend inward, towards bow portion 12. Pinching member 54 presses tube 18 against inner surface 30' of bow portion 12, occluding the passage of fluid through the tube. Deflection of bow portion 12 as linkage portion 14 is moved from the unoccluded position to the occluded position provides driving force for complete occlusion of the tube.

A further alternative embodiment of the present invention is shown in FIGS. 10–12. Alternative occluder 100 is of unitary construction. This alternative design provides he advantage of ease of manufacture, but requires a highly resilient material for extended use, as it depends on three "living hinges" in the place of the rotating snap-fit arrangement of occluder 10.

Alternative occluder 100 has a bow portion 102 and linkage portion 104 formed as a continuous body. The bow portion 102 and linkage portion 104 are defined by living hinges 106 and 108 which are portions of reduced thickness, as in occluder 10. A third living hinge 107, between hinges 106 and 108, allows the linkage portion 104 to be deformed towards the bow portion 102.

Occluder 100 has a pinching member 110 that extends from the linkage portion 104, which contacts the tube to be occluded. An occlusion is created by depression of actuator member 112, which extends from the linkage portion 104 away from the bow portion. The bow portion 102 is also provided with a longitudinal ridge 116, against which the tube will be pressed. Occluder 100 also may have a tube guide member 114 that extends from the linkage member 104 into the passageway 120 defined by the bow portion 102 and linkage portion 104. The tube guide member 114 actually passes through the passageway 120 and through a slot 118 provided in the bow portion 102.

FIG. 11 illustrates occluder 100 in the open, relaxed state. A portion of tubing is shown in cross-section as 122. The tube guide member 114 ensures that the tubing remains proximate to the pinching member 110 and the ridge 116, so that the tube will be occluded by being compressed between them, as shown in FIG. 12. To occlude the tube 122, the actuator member 112 is depressed, either manually or in cooperation with the structure of an infusion pump apparatus. As shown in FIG. 12, the actuator member 112 is depressed from the right to the left and towards the bow portion 102. This movement causes pinching member 110 to compress tube 122 between it and ridge 116 of the bow portion. Tube guide member 114 prevents tube 122 from slipping away from the pinching member 110 and ridge 116.

The design of occluder 100 allows for two stable positions, open (shown in FIG. 11), and closed (shown in FIG. 12). The open position is the relaxed state of occluder 100, which allows for flow of liquid through a tube placed in the passageway 120. The closed position is also stable, as the force applied to the actuator member 112 causes the linkage portion 104 to snap inward, bending at all three hinges 106, 107, and 108, and locking into the closed position.

While the particular embodiments of the tube occluder described and shown herein are fully capable of obtaining the objects and providing the advantages stated above, it is to be understood that they are merely illustrative of the presently preferred embodiments of the invention and that no limitations are intended to the details of construction or design herein shown other than as described in the appended claims.

We claim:

1. A tube occluder, comprising:
   a first portion having opposite ends;
   a second portion extending between the ends of said first portion to define a passageway between the first portion and the second portion for receiving a tube to be occluded;
   said second portion further comprising a pinching member extending from said second portion into said passageway;
   said second portion further comprising at least one hinge portion adapted to allow said second portion to bend and permit said pinching member to move closer to said first portion, thus reducing the size of said passageway to occlude a tube received therein; and
   a tube guide including a guide-eye portion mounted on a linkage portion, said linkage portion extending from the first portion such that said guide-eye portion aligns and holds a tube passed therethrough between said pinching member and said first portion.

2. The tube occluder of claim 1, wherein said second portion is made from a resilient material and has a predetermined thickness, and said at least one hinge portion is an area of said second portion between said opposite ends with a reduced thickness.

3. The tube occluder of claim 2, wherein said first and second portions are separate pieces with said opposite ends of the first portion defining recesses each receiving an end of the second portion to form articulations.

4. The tube occluder of claim 3, wherein the second portion has greater resiliency than the first portion.

5. The tube occluder of claim 2, wherein said first and second portions are integrally formed together, said opposite ends being defined by second and third hinge portions having a reduced thickness as compared to adjoining sections.

6. The tube occluder of claim 1, wherein said linkage portion further comprises an actuator member extending from said linkage portion to facilitate manual depression of said linkage member.

7. A tube occluder, comprising: a bow portion having first end and a second end;
   a linkage portion having a first end and a second end; and,
   a tube guide portion having a coupling portion and a guide-eve portion adapted to receive a tube therethrough and secure the tube in place;
   said linkage portion engaging the bow portion at said first and second ends to define a passageway between the bow portion and the linkage portion adapted to receive a tube therethrough with the tube held in place by the guide-eye portion;
   said linkage portion further comprising a hinge portion between said ends, said hinge portion permitting the linkage portion to bend towards the bow portion, reducing the size of said passageway and occluding a tube received therethrough;
   said coupling portion extending laterally from side bow portion to position said guide-eye portion to direct a tube between said bow portion and said linkage portion.

8. The tube occluder of claim 7, wherein said linkage portion further comprising a pinching member extending from said linkage portion into the passageway between said bow portion and said linkage portion.

9. The tube occluder of claim 7, wherein the first and second ends of said linkage portion are substantially cylindrical.

10. The tube occluder of claim 9, wherein the first and second ends of said bow portion comprise mating receptacles for the first and second ends of said linkage portion.

11. The tube occluder of claim 7, wherein said linkage portion further comprises an actuator member extending outward from said linkage portion in a direction away from the bow portion to facilitate cooperation with and automatic depression of said linkage member by associated structure of a pump apparatus.

12. The tube occluder of claim 7, wherein said bow portion has an outer surface facing away from said linkage portion; and said outer surface further comprises a raised longitudinal rib.

13. The tube occluder of claim 7, wherein said bow portion is manufactured of a substantially rigid plastic material.

14. The tube occluder of claim 7, wherein said linkage portion is manufactured of a resiliently deformable material.

15. A tube occluder comprising:

a L-shaped first portion having two opposite ends;

a second portion extending between the ends of said first portion and defining a plane which a tube for occlusion will intersect;

said first portion further comprising a platform for seating said tube for occlusion, said platform intersecting said plane and being parallel to said tube;

said linkage portion further comprising a pinching member, adapted to occlude said tube, extending from said second portion along said plane toward said first portion;

said linkage portion further comprising at least one hinge portion, said at least one hinge portion adapted to allow said linkage portion to bend and permit said pinching member to move closer to said platform;

said first portion further comprising a tube guide portion having at one end a guide-eye, said guide portion extending adjacent to the space defined by extending said plane into a third dimension along the direction of the tube such that said guide-eye directs the tube along said platform and beneath said pinching portion, such that when said pinching portion moves toward said platform said tube is occluded.

16. The tube occluder of claim 15, wherein said second portion is made from a resilient material and has a predetermined thickness, and said at least one hinge portion is an area of said linkage portion between said opposite ends with a reduced thickness.

17. The tube occluder of claim 16, wherein said first and second portions are separate pieces with said opposite ends of the first portion defining recesses each receiving an end of the second portion to form articulations.

18. The tube occluder of claim 17 wherein the second portion has greater resiliency than the first portion.

19. The tube occluder of claim 15, wherein said second portion further comprises an actuator member extending from said second portion to facilitate manual depression of said linkage member.

20. The tube occluder of claim 15, wherein said second portion further comprises actuator member extending from said second portion to facilitate cooperation with an associated pump apparatus such that when the pump is pumping the tube remains unoccluded and when the pumps is not pumping the tube is occluded.

* * * * *